United States Patent [19]
Khouri

[11] Patent Number: 5,653,744
[45] Date of Patent: Aug. 5, 1997

[54] DEVICE AND METHOD FOR VASCULAR ANASTOMOSIS

[75] Inventor: Roger K. Khouri, St. Louis, Mo.

[73] Assignee: Khouri Biomedical Research, Inc., St. Louis, Mo.

[21] Appl. No.: 429,897

[22] Filed: Apr. 27, 1995

[51] Int. Cl.$^6$ ............................................. A61F 2/06
[52] U.S. Cl. ............................... 623/1; 623/6; 623/11; 623/12; 606/8; 606/139; 606/148; 606/149; 606/154; 606/194; 128/898
[58] Field of Search ........................... 606/194, 154, 606/8, 139, 148, 149; 623/1, 6, 12, 15, 11; 128/898

[56] References Cited

U.S. PATENT DOCUMENTS

| | | | |
|---|---|---|---|
| 3,908,662 | 9/1975 | Razgulov et al. | 606/155 |
| 4,770,176 | 9/1988 | McGreevy et al. | 623/12 |
| 4,930,674 | 6/1990 | Barak | 227/179 |
| 5,141,516 | 8/1992 | Detweiler | 606/154 |
| 5,254,113 | 10/1993 | Wilk | 623/12 |
| 5,274,074 | 12/1993 | Tang et al. | 623/15 |
| 5,276,015 | 1/1994 | Khouri et al. | 514/12 |
| 5,464,450 | 11/1995 | Buscemi et al. | 623/6 |

OTHER PUBLICATIONS

*Microvascular Anastomoses Utilizing New Intravascular Stents* by Moskovitz et al., Ann Plast Surg, vol. 32, pp. 612–618, 1994.

*Sutureless Vasovasostomy: New Technique Using Experimental Microclip in Rat Model* by Gaskill et al., Urology, vol. 40, No. 2, 191–4, 1992.

*A New Method for Microvascular Anastomosis: Report of Experimental and Clinical Research* by Kirsch et al., The American Surgeon, vol. 12, No. 58, pp. 722–727, 1992.

*Experimental Study on Microvascular Anastomosis Using a Dissolvable Stent Support in the Lumen* by Cong et al., Microsurgery, vol. 12, pp. 67–71, 1991.

*Microvascular Anastomosis Using Polyethylene Glycol 4000 and Fibrin Glue* by Kamiji et al., British Journal of Plastic Surgery, vol. 42, pp. 54–58, 1989.

*The Temporary Stent Technique: An Easier Method of Micro–Venous Anastomosis* by Wei et al., British Journal of Plastic Surgery, vol. 35, pp. 92–95, 1982.

*Primary Examiner*—John G. Weiss
*Assistant Examiner*—Francis K. Cuddihy
*Attorney, Agent, or Firm*—Howell & Haferkamp, L.C.

[57] ABSTRACT

A temporary stent and method for vascular anastomosis are disclosed. The method comprises placing, in a vessel to be anastomosed, a stent comprising a biocompatible material; applying staples to anastomose the vessel; and converting the stent material into a liquid that is miscible with blood by melting with warmed saline or pulsed radiation. Also disclosed is a method and composition for delivery of a drug that prevents thrombus formation and/or intimal hyperplasia at the anastomosis.

14 Claims, 1 Drawing Sheet

DEVICE AND METHOD FOR VASCULAR ANASTOMOSIS

BACKGROUND OF THE INVENTION (1) Field of the Invention

This invention generally relates to the field of reconstructive vascular surgery and, more particularly, to a device and method for vascular anastomosis.

(2) Description of the Related Art

Since the first successful vascular anastomosis was performed at the turn of the century, the search for an easier and faster technique than conventional needle-and-thread suturing has challenged surgeons. Payer was the first to describe a technique for sutureless vascular anastomosis using a magnesium ring. (Metalles in den Chirurgie. *Arch. Kiln. Chir.* 62:67, 1900). This principle was modified by Nakayama et al. and further modified by Östrup and Berggren into an apparatus for microvascular anastomosis which is commonly used today. (Nakayama et al., *Surgery* 52:918–931, 1962; First Scandinavian Seminar on Reconstructive Microsurgery, Gothenburg, Sweeden, October 1979, pp. 521–525, 1986. Although this apparatus has a number of advantages, it is still far from the ideal vascular anastomosis device. The wall of the arteries is usually too thick and rigid to permit the necessary vessel eversion. This problem is even more severe in diseased vessels and limits the use of this device in vascular surgery. Furthermore, the device is quite cumbersome and the surgical methods required for its use are difficult to master. Nonetheless, for lack of anything better, and because it saves operating time, the device is routinely used today in microvascular free flap surgery to anastomose veins.

An alternative to suturing the vessel, is the use of tiny staples or microvascular clips to bring vessel edges together circumferentially. (For example see Kirsch et al, *The American Surgeon* 12:722–727, 1992, which is incorporated herein by reference). Use of these staples is, however, limited by the problem that in order to achieve accurate placement of the staples, eversion of the edges of the vessel wall, and the avoidance of a "backwall" bite, an assistant is required to hold the vessel edges up while the staples are inserted. Not only is this inconvenient, such assistance is not always possible such as, for example, in endoscopic procedures.

The use of stents in vascular reconstruction can both facilitate the procedure itself and improve the outcome, particularly in small vessels and in veins. Temporary stents have been used in vascular surgery that are removed prior to complete closure of the anastomosis. These have been reported to improve the ease and rapidity of the anastomosis as well as decrease the danger of injury to the lumen and posterior wall and improve the percent of anastomoses remaining patent. (Wei et al., *British J Plastic Surg* 35:92–95, 1982, which is incorporated herein by reference). Soluble intravascular stents that dissolve and need not be removed have also been reported. Kamiji et al. used a polyethylene glycol stent that reportedly is washed away by the blood flow and dissolved after restoring blood flow. (*British J Plastic Surg* 42:54–58, 1989, which is incorporated herein by reference). In addition, stents have been reported that, upon completion of the anastomosis, can be melted or dissolved by warm isotonic saline and subsequently washed away in the blood on restoring blood flow (Cong et al, *Microsurgery* 12:67–71, 1991; Moskovitz et al, *Annals Plastic Surgery* 32:612–618, 1994, which are incorporated herein by reference). These groups used stents composed of a mixture of mono-, di-, and triglycerides that melt at temperatures near body temperature. Because the glycerides are normal elements in the blood stream, the stent was considered biocompatible.

Particular advantages reported on use of the stent with suturing of the anastomosis were an improvement in the accuracy and speed of the procedure, the minimizing of minor trauma, the avoidance of suture errors such as a partial bite of the opposite wall, the achieving of a better coaptation of cut edges, the avoidance of narrowing at the anastomosis sites, the achieving of even distribution between stitches, and the preventing of vasospasm (Cong et al., 1991). Use of the stent with fibrin glue was reported to have the disadvantage of producing aneurysms. Although one group used the stent in combination with sutures, neither used the stents in combination with staples. Use of staples would be expected to reduce the likelihood of aneurysm formation compared to the use of fibrin glue because of the staples firmly holding the media in close enough apposition to allow proper healing over time. Furthermore, staples would be expected to decrease the time required for the procedure compared to use of suturing with the stent.

The use of a stent in combination with staples has not been appreciated as an advantage over the staples alone in open field microvascular anastomosis inasmuch as it has been reported that a stent is not necessary with microclip anastomosis (Kirsch et al, 1992). In the non-vascular anastomosis of vasovasostomy, an absorbable stent was used in combination with microvascular clips. (Gaskill et al, *Urology* 40:191–194, 1992, which is incorporated herein by reference). The stent was hollow and composed of polyglycolic acid. Furthermore, the stent was not immediately absorbable as would be required for such a temporary stent in a vascular anastomosis. This group reported that the combination of an absorbable stent with microclips allowed a shorter time for completion of the procedure (7.6 v. 8.5 minutes) and required less care. Nevertheless, it was indicated that there was no advantage to using the stent because of a high percentage of granulomas following its use apparently resulting from the need for more clips to seal the anastomosis or from obstruction of the stent. The requirement for more clips may indicate a failure of the stent to fit snugly into the vessel. Furthermore, obstruction from the stent is likely to have been a result of the stent dissolving over a relatively long period of time. Moreover, this reference did not apply the technique using the slowly absorbable stent along with stapling to vascular anastomosis.

Thus, in performing a vascular anastomosis, it would be desirable to have an improved method that is easy and rapid and that does not require an expert surgical assistant and that also produces an eversion of the vessel edges and avoids a "backwall" bite.

One of the problems that can be associated with vascular anastomosis is the formation of thrombus at the anastomosis. The thrombus results from a gradual accumulation of platelets at the anastomosis and the formation of fibrin. The thrombus thus formed could eventually occlude the vessel. It would be desirable, therefore, to provide some means to diminish the likelihood of formation of a thrombus at the anastomosis site.

SUMMARY OF THE INVENTION

In view of the limitations with existing methods, Applicant has succeeded in devising an improved device and method for vascular anastomosis. The method comprises the steps of placing, in vessels to be anastomosed, a stent comprising a biocompatible material; applying staples to anastomose the vessels; and converting the stent material into a liquid that is miscible with blood by melting with warmed saline, pulsed radiation or otherwise.

In accordance with the present invention, it has been discovered that utilization of a temporary stent for vascular anastomosis holds the vessel edges approximated together and stabilizes them while functioning as an anvil against which the stapler can safely apply pressure without fear of catching the posterior wall. The stent is also designed in a shape that tends to cause eversion of the vessel edges and facilitates approximation of intima to intima. The stent is made of a biocompatible material which is rapidly melted upon applying heat, pulsed radiation such as laser energy or U.V. light, etc. and completely miscible with blood on flushing out the anastomosis by restoring blood flow.

Surprisingly, the method could be performed by a novice in substantially less time than the conventional suture anastomosis could be performed by an expert. Furthermore, anastomoses performed using the stent with staples showed excellent approximation of the intimal edges and no significant anastomotic stenosis.

Thus the present invention provides the vascular surgeon with new and improved procedure for performing vascular anastomosis that is faster and easier to perform and that provides an excellent outcome. This new method is particularly applicable to endoscopic procedures where the otherwise extremely difficult sutured anastomosis can now be replaced with an easier, faster and safer anastomosis using staples available and well known in the art combined with a stent. In addition, the new method herein provides the vascular surgeon with an approach that can be used for end-to-side anastomoses by using a T-shaped or Y-shaped stent.

Furthermore, the stent could also function as a drug delivery device. Thus, the present invention is also directed to a stent for use in vascular anastomosis comprising a substance that prevents thrombus formation as well as to a method for preventing thrombus formation at a site of vascular anastomosis in an individual comprising administering to the individual a substance that prevents thrombus formation. The incorporation of the drug into the stent would allow a continuous release of the drug once placed in the lumen during the anastomosis procedure. Then upon melting and dissolving or emulsifying the anastomosis, the drug within the stent would be immediately released.

Among the several advantages found to be achieved by the present invention, therefore, may be noted the provision of a method of vascular anastomosis for improved accuracy and speed compared to use of the stent alone or with suturing or compared to stapling alone; the provision of a method of vascular anastomosis that avoids the danger of injury to the lumen or posterior wall from the staples; and the provision of a method and device for vascular anastomosis that utilize a stent to deliver a bioactive drug to prevent undesirable complications such as the formation of thrombus or intimal hyperplasia.

While the principal advantages and features of the present invention have been described above, a more complete and thorough understanding of the invention may be attained by referring to the drawings and description of the preferred embodiment which follow.

DESCRIPTION OF PREFERRED EMBODIMENTS

Figure 1:
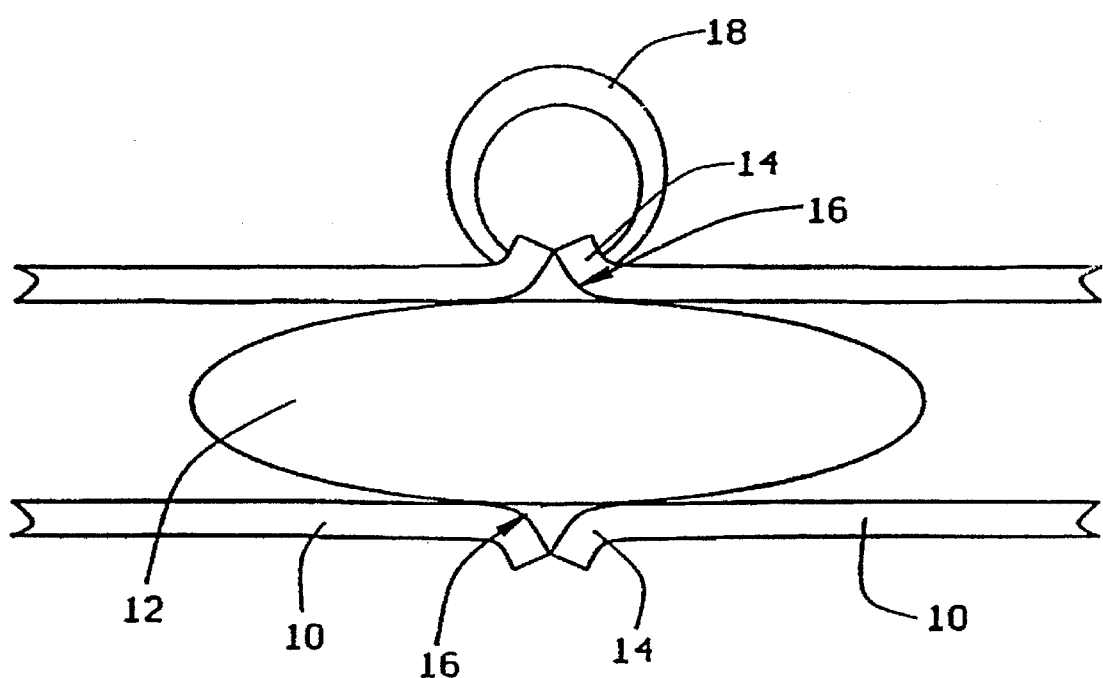
FIG. 1 illustrates use of the stent and staples of the present invention in vascular anastomosis.

As shown in FIG. 1, a stent 12 is placed in the lumen of vessel 10. The stent has an oval shape in which the longitudinal axis length is greater than the transverse axis length. Thus, there is a lengthwise tapering from the center to the end. This design effectively causes an eversion of the edges 14 of the vessel 10 to facilitate approximation of the intima 16 of each of the two edges. This is explained in greater detail, infra. Staple 18 pinches together the edges 14 of the vessel 10 bringing together the intima 16.

The stent material as placed in the lumen of the vessels is solid and must be of sufficient strength to be able to act as an anvil against which the staples are applied. By applying the staples against the stent, the likelihood of penetration of the staple into the lumen and injury to the inner lining of the vessel wall is diminished. Furthermore, the stent prevents a deeper penetration to the posterior wall on opposite side of the vessel lumen thus precluding backwall injury.

The stent can be made up of any solid material, which upon completion of the anastomosis, can be rapidly melted or dissolved and that is readily miscible with blood upon restoring flow through the anastomosis.

The melting or dissolving of the stent can be accomplished by any suitable means, for example by irrigating the operative field with warmed saline. Alternatively, the stent material can be melted by pulsed radiation such as with a laser, U.V. light, or by any other means that can convert the solid stent material into a liquid.

Examples of stent materials useful in the present invention are mixtures of mono-, di- and triglycerides, polyglycolic acids and polyethylene glycol. The stent materials are readily miscible with blood either by virtue of being water soluble or by being readily able to form an emulsion or dispersion with blood. Polyethylene glycol 1500, which is water soluble and melts between 44° C. and 48° C. is an example of stent material useful in the present invention. A preferred stent material is a mixture of mono-, di- and triglycerides that consists mostly of triglycerides with diglycerides present in a concentration of 15% or less and monoglycerides present in a concentration of 1% or less. This mixture is sold under the trademark WITEPSOL® and the manufacturer's identification H 37 (Hüls, A. G., Witten, Germany; Hüll America, Piscataway, N.J.). WITEPSOL® H 37 comprises glycerol esters of vegetable saturated fatty acids, mainly lauric acid prepared from coconut and palm kernel oils. (See Hüls WITEPSOL® product bulletin which is incorporated by reference). It is a solid with a melting point between 36° C. and 38° C. Saline warmed to approximately 45° C. rapidly melts this material.

The stent material must also be biocompatible. In addition, the liquid stent material by virtue of being readily dissolved, emulsified or dispersed in the blood, produces no deleterious effect upon restoring blood flow and flushing from the anastomosis.

The stent materials disclosed above are exemplary only and the skilled artisan will appreciate that stents within the scope of this invention can be comprised of any suitable material that satisfies the criteria set forth above.

Methods for preparation of stents are well known in the literature. (See for example Cong et al., *Microsurgery* 12:67–71, 1991; Moskovitz et al, *Ann Pastic Surg* 32:612–618, 1994; Kamiji et al., *Brit J Plastic Surg* 42:54–58, 1989, which are incorporated herein by reference). Stents can be fabricated in virtually any desired size, although the shape and size depicted in the preferred embodiment has been found to be particularly helpful in everting the vessel sidewalls.

The stent for use in anastomosis of a particular vessel is selected so that it will fit snugly inside the lumen of that vessel. As shown in the figure, as the stent is inserted into the vessel, its sidewalls eventually contact the stent and are angled obliquely, or radially outward. After insertion into both ends, the vessel sidewalls contact each other obliquely and are readily everted upon further advance.

Staple, 18, can be any of a number well known in the art and devices for applying staples are also well known in the art. (See for example Kirsch et al, Am Surgeon 58:722-727, 1992; Tredway et al., Fertil Steril 62:624-629, 1994, which are incorporated herein by reference). The staples can be made of any biocompatible material such as, for example, titanium. The size of the staples is selected according to the wall thickness of the vessel being anastomosed and in the range of can be in the range of from approximately 0.3 mm to approximately 2 mm. The present invention is applicable to anastomosis of vessels of virtually any size including vessels as large as the abdominal aorta as well as vessels as small as 1 mm in diameter and smaller. The methods and compositions herein are also applicable to both arteries and veins.

Vascular anastomosis performed by the present improved procedure is faster and easier to perform while providing an excellent outcome. Because of this, the present improved method facilitates the performance of otherwise extremely difficult anastomosis procedures. For example, the present invention provides a practical method for endoscopic vascular surgery. The method can also be used with L-shaped or T-shaped stents for use in end-to-side anastomosis. This provides a practical method for coronary artery bypass grafts where an end-to-side anastomosis is desired.

The stent can also act as a means to locally deliver bioactive agents that have beneficial effects upon the anastomosis. The incorporation of a drug into the stent would allow local release of the drug during the anastomosis procedure and particularly upon the melting and dissolution or emulsion of the stent inside the anastomosis. This provides a very practical method for direct delivery of the drug to the anastomosis. One example of such a bioactive agent that can be incorporated into the stent for delivery to the anastomosis is recombinant Tissue Factor Pathway Inhibitor (TFPI). TFPI reduces the buildup of thrombus at the anastomosis, improves the patency rate of the vascular anastomosis (Khouri et al., U.S. Pat. No. 5,276,015 which is incorporated by reference). The inventor also believes that TFPI can reduce the amount of intimal hyperplasia which develops at vascular anastomoses. The incorporation of such an agent into the stent material would represent an ideal method of local drug delivery.

The above disclosure Generally describes the present invention. A more complete understanding can be obtained by reference to the following specific examples which are provided herein for purposes of illustration only and are not intended to be limiting unless otherwise specified.

EXAMPLE 1

The preparation of stents is illustrated in the method used for making the 10 mm stents.

Stents having a diameter of 10 mm were fabricated from 1 g WITEPSOL® H 37. WITEPSOL® H 37 is a solid with a melting point between 36° and 38° C. It is widely used in pharmaceuticals for drug delivery. The pastilles were carefully warmed up to 45° C. in a water bath and the resulting clear fluid brought into silicone molds. The molds were in a generally oval shape providing a tapering of the two ends of the stent. The material was allowed to cool down and harden at room temperature. The stents were removed from the mold, gas sterilized and stored at −20° C. On the day of surgery, the stents were kept in an ice-saline bath until they are inserted into the vessel ends.

EXAMPLE 2

This example illustrates the method of anastomosis of large and small vessel using the abdominal aorta and small arteries in pigs and rabbits.

In 5 American farm pigs (30 kg), a median laparotomy was performed and the abdominal aorta was dissected transperitonially and divided between vascular clamps. A 10 mm stent of WITEPSOL® H 37 (1 g) was inserted into the divided vessel stumps. The shape of the stent was such that it caused a slight eversion of the edges and facilitated intimal approximation. In the first experiment the anastomosis was performed by applying approximately 20 staples with Endopath EAS. In the following 4 experiments, the anastomoses were performed with Endopath EMS and a smaller number of staples was required. The experiments were performed by the operator alone, without an assistant holding the vessel edges. At the completion of the anastomoses, the operative field was irrigated with warm saline (45° C.) until the stent completely dissolved (10–15 seconds). The clamps were released and the anastomoses were observed for 60 minutes. The animals were sacrificed with an overdose of barbiturates and a lead oxide angiography was performed. The abdominal aorta, including the anastomosis was then resected and submitted for histological evaluation.

Abdominal aortas (3 mm), carotid arteries (2 mm), and central ear arteries (1 mm), were dissected in New Zealand white rabbits and divided between vascular clamps. In 5 animals a conventional sutured anastomosis was performed by a single experienced microsurgeon without an assistant. In 5 animals a stented and stapled anastomosis was performed by a single novice microsurgeon without an assistant and without prior experience with the use of the stapler. To perform the stented and stapled anastomosis, the vessels were approximated over the stent and held together by applying 8 microstaples around the circumference. The stents were made of an inert triglyceride compound (WITEPSOL® H 37), which melts at body temperature. They were designed such that they fitted snugly inside the lumen and caused an eversion of the edges to facilitate intimal approximation. At the completion of the anastomoses, the vessels were irrigated with warm saline (45° C.) until the stents completely dissolved (10–15 seconds), and the clamps were then released. The time taken to complete the anastomosis (clamp on/clamp off), and one day and one week patency were recorded. Angiograms were performed and the vessels were perfusion fixed at one week to determine the presence of anastomotic stenosis. Using T-shaped stents, end-to-side anastomoses were performed and compared with similar sutured anastomoses.

All anastomoses were patent at one day and one week. The average time taken by the novice to perform the stapled anastomosis alone was 2.5 minutes. In contrast, it took the experienced vascular surgeon 9 minutes to perform the sutured anastomoses ($p<0.01$). All the stapled anastomoses had excellent approximation of the intimal edges without significant anastomotic stenosis. There was no observable side effect from the stent material.

These experiments demonstrate the stapled vascular anastomosis using a soluble intraluminal stent that acts as an anvil. The presence of a stent made the stapling very practical and simple. The stent is made up of a solid material which can dissolve on command at the completion of the anastomosis. There were no observed deleterious effects from the bolus of lipid infusion which resulted when the lipid stent dissolved, although other potential materials could be found which can become soluble by pulsed radiation or other physical means.

In view of the above, it will be seen that the several objects of the invention are achieved and other advantageous results attained.

As various changes could be made in the above constructions without departing from the scope of the invention, it is intended that all matter contained in the above description shall be interpreted as illustrative and not in a limiting sense.

What is claimed is:

1. A method for vascular anastomosis in a subject comprising the steps of:
   (a) first, placing, in a vessel to be anastomosed, a stent comprising a biocompatible material;
   (b) second, applying staples to evert the edges of the vessel by pressing the staples against the vessel edges to thereby use the stent as an anvil to anastomose the vessel; and
   (c) third, converting the stent into a liquid that is miscible with blood.

2. The method according to claim 1 wherein the stent comprises a material which melts upon applying heat and the step of converting the stent to a liquid includes the step of applying heat.

3. The method according to claim 2 wherein the step of applying heat includes the step of irrigating the anastomosed vessel with warmed saline.

4. The method according to claim 3 wherein the stent comprises a material selected from the group consisting of a mixture of monoglycerides, diglycerides and triglycerides; a polyglycolic acid; a polyethylene glycol; and mixtures thereof.

5. The method according to claim 4 wherein the stent material comprises WITEPSOL® H 37.

6. The method according to claim 1 wherein the stent comprises a material which melts on applying pulsed radiation and the step of converting the stent to a liquid includes the step of applying pulsed radiation.

7. The method according to claim 6 wherein the stent comprises a material selected from the group consisting of a mixture of monoglycerides, diglycerides and triglycerides; a polyglycolic acid; a polyethylene glycol; and mixtures thereof.

8. The method according to claim 1 wherein the anastomosis is an end-to-end anastomosis and the stent has a center and two opposite ends, and a lengthwise tapering from the center to each end.

9. The method according to claim 1 wherein the anastomosis is an end-to-side anastomosis and the stent is in an L-shape, a T-shape or a Y-shape.

10. The method according to claim 1 wherein the stent contains a substance that prevents thrombus formation or intimal hyperplasia.

11. The method according to claim 10 wherein the substance that prevents thrombus formation or intimal hyperplasia comprises Tissue Factor Pathway Inhibitor (TFPI).

12. A method for vascular anastomosis in a subject comprising the steps of:
   (a) first, everting the vessel edges by advancing a stent comprising a biocompatible material into the vessel to be anastomosed;
   (b) second, applying staples to the everted edges of the vessel by pressing the staples against the vessel edges to thereby use the stent as an anvil to anastomose the vessel; and
   (c) third, converting the stent into a liquid that is miscible with blood.

13. The method according to claim 12 wherein the stent has a portion with a cross-sectional area sized to fit snugly within said vessel.

14. The method according to claim 13 wherein the stent has a center and two opposite ends, and a lengthwise tapering from the center to each end, said center comprising said snugly fitting portion.

* * * * *